United States Patent [19]

Campbell et al.

[11] Patent Number: 5,163,989
[45] Date of Patent: Nov. 17, 1992

[54] METHOD FOR FORMING A BALLOON MOLD AND THE USE OF SUCH MOLD

[75] Inventors: Peter F. Campbell, San Jose; Timothy J. Ryan, Los Gatos, both of Calif.

[73] Assignee: Advanced Cardiovascular Systems, Inc., Santa Clara, Calif.

[21] Appl. No.: 573,534

[22] Filed: Aug. 27, 1990

[51] Int. Cl.$^5$ .................................. B29C 57/00
[52] U.S. Cl. .................................. 65/110; 65/102; 264/221; 264/317; 264/571; 264/573
[58] Field of Search ........... 264/225, 226, 227, 221, 264/219, 317, 510, 511, 512, 571, 573; 604/96; 65/110, 102, 108

[56] References Cited

U.S. PATENT DOCUMENTS

| | | | |
|---|---|---|---|
| Re. 32,983 | 7/1989 | Levy | 264/573 |
| 2,782,459 | 2/1957 | Moncrieff | 264/573 |
| 3,459,175 | 8/1969 | Miller | 604/96 |
| 3,774,596 | 11/1973 | Cook | 604/96 |
| 3,849,531 | 11/1974 | Mofford | 264/573 |
| 4,093,484 | 6/1978 | Harrison et al. | 264/573 |
| 4,141,364 | 2/1979 | Schultze | 604/96 |
| 4,261,339 | 4/1981 | Hanson et al. | 604/96 |
| 4,304,586 | 12/1981 | Vrijssen et al. | 65/110 |
| 4,311,659 | 1/1982 | Rey et al. | 264/221 |
| 4,406,656 | 9/1983 | Hattler et al. | 604/96 |
| 4,411,055 | 10/1983 | Simpson et al. | 264/573 |
| 4,448,195 | 5/1984 | LeVeen et al. | 604/100 |
| 4,459,977 | 7/1984 | Pizon | 604/102 |
| 4,655,745 | 4/1987 | Corbett | 604/96 |
| 4,681,092 | 7/1987 | Cho et al. | 604/96 |
| 4,748,982 | 6/1988 | Horzewski et al. | 604/102 |
| 4,787,388 | 11/1988 | Hofmann | 604/194 |
| 4,848,344 | 7/1989 | Sos et al. | 604/96 |
| 4,909,979 | 3/1990 | Possis et al. | 264/571 |
| 4,941,877 | 7/1990 | Montano, Jr. | 604/96 |
| 4,952,357 | 8/1990 | Euteneur | 264/255 |
| 4,963,313 | 10/1990 | Noddin et al. | 264/512 |

FOREIGN PATENT DOCUMENTS 0331040 6/1989 European Pat. Off. .

Primary Examiner—Jay H. Woo
Assistant Examiner—Robert B. Davis
Attorney, Agent, or Firm—Crosby, Heafey, Roach & May

[57] ABSTRACT

A mold and method for forming a balloon for dilatation catheters, particularly balloons with a prismlike shape with a transverse polygonal cross section when the internal pressure is at atmospheric conditions. Upon inflation to higher internal pressures, the balloon assumes a normal circular cross section. The balloon shape is particularly suitable for balloons formed of polyethylene terephthalate and the like which are not readily heat settable. Reduced deflated profiles are obtained. The mold is formed by first making a preformed core member which has the shape and dimensions which are desired for the balloon. A heat-formable tubular member, preferably formed of borosilicate glass such as PYREX, is disposed about the core member, subjected to heat and an internal vacuum so as to be shaped onto the exterior of the core member. Once shaped, the tubular member is allowed to cool and set, the core member is dissolved away, leaving the shaped glass mold having an internal molding chamber with the desired shape and dimensions for the inflatable balloon.

9 Claims, 2 Drawing Sheets

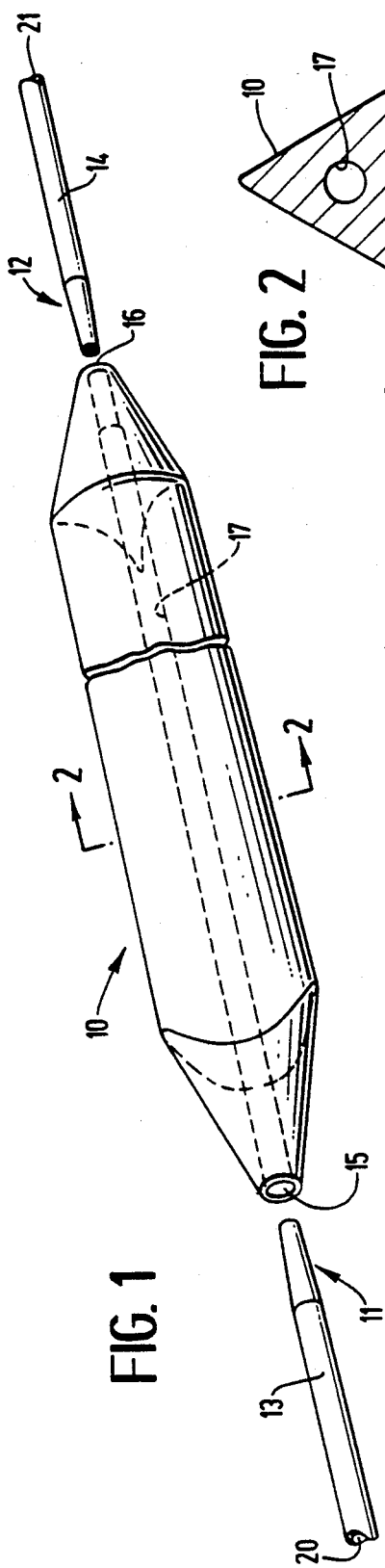
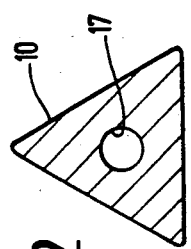
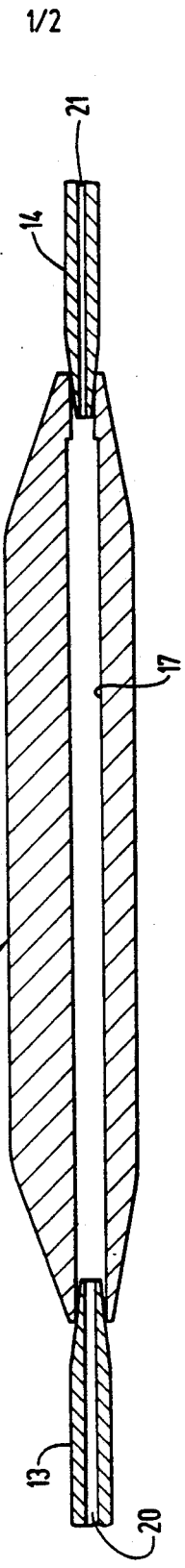
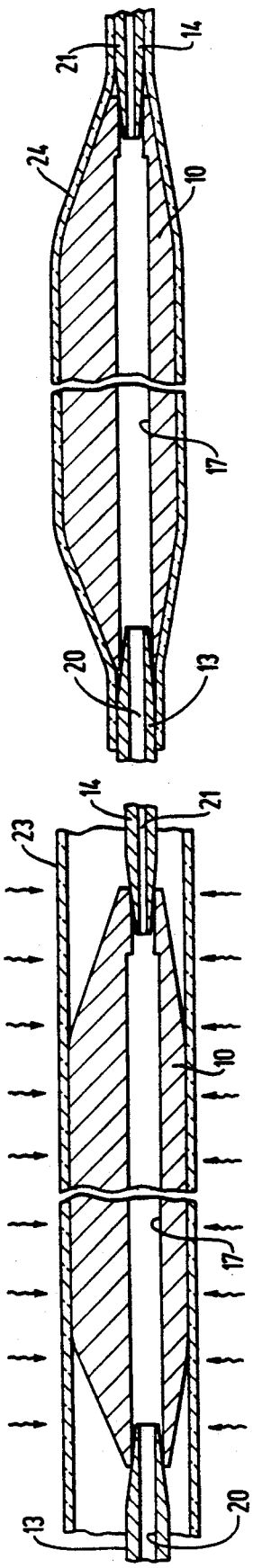

METHOD FOR FORMING A BALLOON MOLD AND THE USE OF SUCH MOLD

BACKGROUND OF THE INVENTION

This invention generally relates to a mold and method for forming small diameter balloons suitable for dilatation catheters such as are used in angioplasty procedures.

In typical percutaneous transluminal coronary angioplasty (PTCA) procedures, a guiding catheter having a preformed distal tip is percutaneously introduced into the cardiovascular system of a patient through the brachial or femoral arteries and advanced therein until the distal tip thereof is in the ostium of the desired coronary artery. A guidewire and a dilatation catheter having a balloon on the distal end thereof are introduced through the guiding catheter with the guidewire slidably disposed within an inner lumen of the dilatation catheter. The guidewire is first advanced out of the distal tip of the guiding catheter and into the patient's coronary vasculature until the distal end of the guidewire crosses the lesion to be dilated. Then the dilatation catheter is advanced out the distal end of the guiding catheter over the previously introduced guidewire until the dilatation balloon is properly positioned across the lesion. Once in position across the lesion, the flexible, relatively inelastic balloon is inflated to a predetermined size with radiopaque liquid at relatively high pressures (e.g., greater than about 4 atmospheres) to radially compress the atherosclerotic plaque of the lesion against the inside of the artery wall to thereby dilate the lumen of the artery. The balloon is then deflated so that the dilatation catheter can be removed and blood flow resumed through the dilated artery.

Further details of angioplasty procedures and the devices used in such procedures can be found in U.S. Pat. No. 4,323,071 (Simpson-Robert); U.S. Pat. No. 4,332,254 (Lundquist); U.S. Pat. No. 4,439,185 (Lundquist); U.S. Pat. No. 4,168,224 (Enzmann et al.) U.S. Pat. No. 4,516,972 (Samson); U.S. Pat. No. 4,538,622 (Samson et al.); U.S. Pat. No. 4,554,929 (Samson et al.); and U.S. Pat. No. 4,616,652 (Simpson) which are hereby incorporated in their entirety by reference thereto.

Steerable dilatation catheters with built-in or fixed guidewires or guiding elements are frequently used because such catheters generally have smaller deflated profiles than conventional dilatation catheters with movable guidewires with equivalent balloon size. The lower deflated profile of these catheters allows them to cross tighter lesions and to be advanced much deeper into the patient's coronary anatomy. Further details of low-profile steerable dilatation catheters may be found in U.S. Pat. No. 4,582,181 (Samson); U.S. Pat. No. 4,619,263 (Frisbie et al.); U.S. Pat. No. 4,641,654 (Samson et al.); U.S. Pat. No. 4,664,113 (Frisbie et al.), U.S. Pat. No. 4,771,778 (Mar) and U.S. Pat. No. 4,793,350 (Mar et al.) which are hereby incorporated in their entirety by reference thereto.

Progress in the development of angioplasty catheters has included significant reductions in the deflated profiles of such catheters which allow them to be advanced through tighter stenoses and much deeper into the patient's coronary anatomy. The use of high-strength materials for the dilatation balloon and other catheter components have aided in this progress by allowing much thinner balloon walls. Biaxially oriented, high-strength plastics such as polyethylene terephthalate (PET) have been found to be particularly effective in this regard. See for example, U.S. Pat. No. 4,456,000 (Schjeldahl et al.).

The prior art dilatation balloons made of polyethylene and the like were usually heat set after forming with the interior of the balloon under a vacuum so that when the balloon is subsequently subjected to a vacuum prior to inserting or removing the dilatation catheter the "wings" of the balloon would curve about an inner member of the catheter assembly. This greatly reduced the effective profile of the balloon and allowed it to be more readily advanced into and withdrawn from the patient's arterial system.

However, many high-strength plastic materials, particularly polyesters such as PET, do not readily heat set so that the wings of the balloon cannot be preshaped to curve around an inner member when the interior of the balloon is subjected to a vacuum. When a balloon made from such polyester material is subjected to a vacuum, the wings thereof generally extend radially away from the inner member forming a substantial profile in at least one plane which can interfere with the advancement and withdrawal of the balloon. This minimizes one of the main reasons for using the high-strength material, namely, reduced deflated profiles. Moreover, the edge of the wings of the deflated balloon may be sharp enough to damage the interior lining of the artery.

In copending application Ser. No. 397,985 filed Aug. 23, 1989 a dilatation catheter is described which has a balloon formed into a prism-like shape with a polygonal transverse cross-section. Preferably, the polygonal cross section has from three to six sides, the triangular and square cross sections being preferred. When the prism-like balloon is inflated to the pressures normally encountered in angioplasty procedures, it expands to a conventional, generally circular transverse cross section to effectively dilate a stenotic region of a patient's artery. When the interior of the balloon of the invention is subjected to a vacuum, the configuration formed has the same number of wings as sides in the polygonal shape, which greatly reduces the span thereof and decreases the effective deflated profile of the balloon. Additionally, the balloon so formed will consistently collapse to the same deflated configuration having three or more wings when a vacuum is applied to the balloon interior.

Prior techniques for the manufacture of the prism shaped balloon included extruding the desired polymer resin into a tubular form, then inflating the tube at elevated temperatures and pressures in a heated mold having an interior surface of the desired shape. The high temperatures allow the pressurized tubing within the mold to expand and take the form thereof. The molds were made in two or more pieces and required very accurate machining of the interior surface thereof in order to form acceptible balloons for angioplasty catheters. However, notwithstanding how accurately the mold was machined, parting lines were molded into the balloon surface at the junctions of the mold sections. These parting lines on the surface of the working portion of the balloon created areas of weakness and also prevented the uniform expansion of the balloon.

What has been needed and heretofore unavailable is a balloon mold and a method of operating a mold which does not generate parting lines in the surface of the final balloon product. The present invention satisfies this need.

SUMMARY OF THE INVENTION

This invention is generally directed to a mold and a method of using such a mold to form an inflatable member, such as a balloon for dilatation catheters and the like which is free of parting lines.

The mold of the invention has a continuous, unbroken inner molding surface defining a molding chamber with inner molding surface corresponding to the desired shape and dimensions for the working and tapered sections of a dilatation balloon. The mold body is preferably formed of a glass or glass like material which is heat shrinkable in order to facilitate making the mold.

To make the balloons, a tubular plastic member is placed within the inner mold chamber, inflated and heated therein so as to be pressed against the inner molding surface and be molded into the desired size and shape thereby. The shaped balloon is cooled to set the size and shape thereof and then is deflated to facilitate removal from the inner molding chamber of the mold.

The mold of the invention is preferably formed by first making a core member from a body with the exterior surface thereof having the desired shape and dimensions for at least the working section and the tapered ends of the balloon. A passageway extends through substantially the entire length of the core and at least one elongated holding member is secured into an opening in one end of the core. Preferably, the elongated holding member has an inner passageway which is in fluid communication with the inner passageway within the core member. Preferably, hollow holding member is secured to each end of the core member and the inner passageways therein are in fluid communication with the inner passageway of the core member.

A heat-formable tubular member, preferably formed of glass, is disposed about the core, heated and subjected to an internal vacuum in order for the tubular member to be shaped onto the core and take the shape and dimensions of the exterior shape thereof. The heat-formed tubular member is cooled to set the material and then the elongated holding members are removed from the core. A solution capable of dissolving the core member is then introduced into the passageway of the core member through the tapered ends of the cooled heated formed member. Preferably, the solution is passed through the interior passageway of the preform until the entire preform is dissolved away.

The set interior of the heat-formed tubular member accurately takes the shape and dimensions of the core and little or no preparation is needed in order to shape balloons therein. To form the balloons a suitable plastic tubular member, sometimes called a parison, is disposed within the glass mold, expanded with a fluid such as nitrogen and heated therein so as to press the expanded portion of the plastic tubular member against the inner molding surfaces. While maintaining the internal fluid pressure within the tubular member, the plastic tubular member is allowed to cool and thereby take the form of the molding surfaces. Once formed into the desired shape and dimensions for the balloon, it may then be deflated and removed from the interior of the mold. The molding surface which shapes the balloon is smooth and continuous, so there are no parting lines on the working or tapered surfaces of the balloon. The balloon is likewise smooth and continuous.

While the mold of the invention is particularly suitable for forming prism-like balloons described in co-pending application Ser. No. 397,985 filed Aug. 23, 1989, it can be readily used for forming balloons of a wide variety of sizes and shapes. The application Ser. No. 397,985 is hereby incorporated herein in its entirety.

These and other advantages of the invention will become more apparent from the following detailed description of the invention when taken in conjunction with the accompanying exemplary drawings.

BRIEF DESCRIPTION OF THE DRAWINGS

FIG. 1 is an exploded perspective view of a balloon mold embodying features of the invention;

FIG. 2 is a transverse cross-sectional view taken along the lines 2—2 shown in FIG. 1;

FIG. 3 is a longitudinal, cross-sectional view of the mold shown in FIG. 1 assembled;

FIG. 4 is a longitudinal, cross-sectional view illustrating the heating of a heat shrinkable tubular member disposed about the core of the mold;

FIG. 5 is a longitudinal, cross-sectional view as shown in FIG. 3 with the heat shrinkable member heat shrunk onto the mold core member;

DETAILED DESCRIPTION OF THE INVENTION

Figure 6:
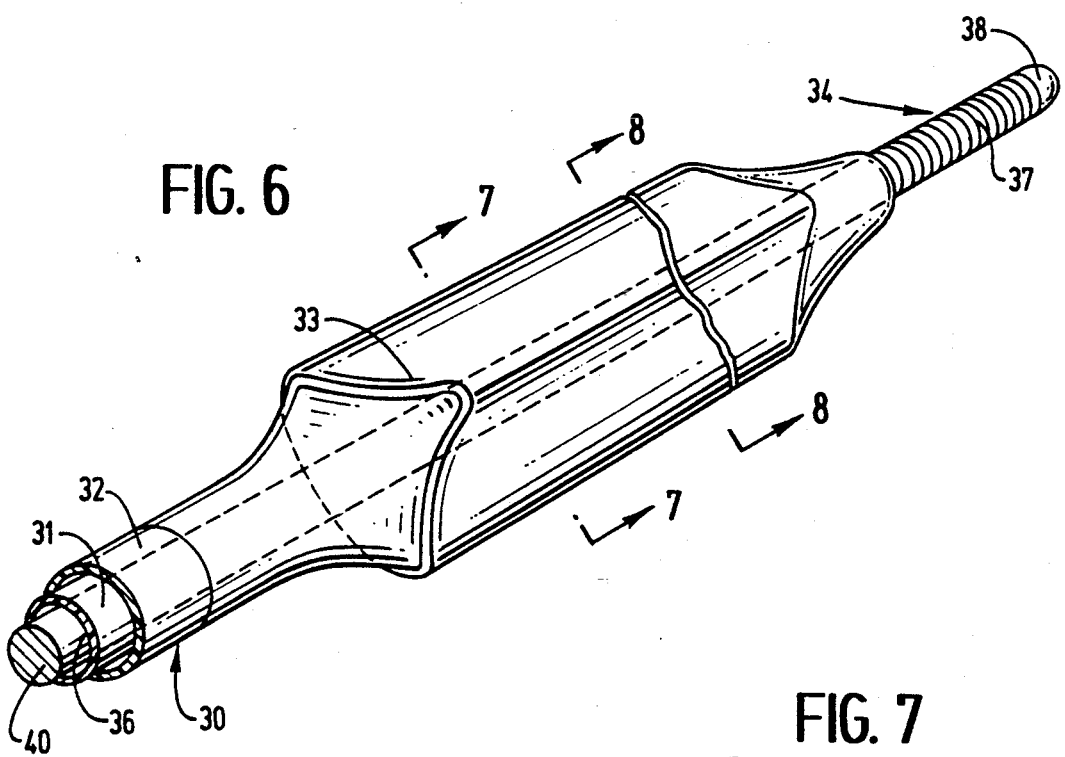
FIG. 6 is a perspective view of a prism-shaped balloon on the distal end of a dilatation catheter which is readily made with a mold and a method embodying features of the invention.

FIGS. 1-4 illustrate the various steps in making a balloon mold in accordance with the present invention. A core member 10 is first formed as shown in FIG. 1 as a preform which provides the mold with the molding shape desired for the central working section and the tapered end sections of the final balloon product. Tapered ends 11 and 12 of elongated holding elements or pins 13 and 14 respectively, are adapted to be fitted (e.g. press fitted) into the open ends 15 and 16 of the core member 10 as shown in FIG. 3. Passageway 17 extends through the interior of the core member 10 and is in fluid communication with the inner lumens 20 and 21 of the tubular holding members 13 and 14. The outer surfaces of the core member 10 and the tubular members 13 and 14 are very finely and accurately machined to the size and shape of the balloon desired, particularly at the junction between the core member and the tubular holding members so as to avoid any parting lines in the final balloon product even on the skirts of the balloon which extend from the ends of the tapered sections.

As shown in FIG. 4, a heat-formable tubular member 23, preferably formed of borosilicate glass, is disposed about the core member 10 and at least partially about the tubular holding members 13 and 14, and then heated and subjected to an internal vacuum to cause the tubular glass member to form onto the core member and the portions of the ends of the tubular holding members secured to the ends of the core member. Upon forming onto the core member 10 and the ends of the tubular holding members 13 and 14, the inner surface of the heat-shrinkable tubular member 23 takes on the shape and dimensions of the exteriors of the core member and the tubular members to form the molding surfaces for the balloon. Upon cooling, the shaped, heat-formed tubular member 23 is the final mold 24 for forming the balloons as illustrated in FIG. 5. FIG. 2 illustrates the cross-section of the core member 10 which forms a preferred balloon transverse cross-sectional shape. Upon cooling the holding pins are removed from the ends of the core member.

To remove the core member 23 from the interior of the mold member 24, a solution capable of dissolving the core member 10 is passed through the inner lumen 17 extending through the core member 10. The solution is passed through the inner passageway 17 until the core member 10 is completely dissolved or the remnants of the core member can be removed manually through the open ends of the mold 24.

The core member 10 should be made from a material which has a relatively small coefficient of expansion, so that there is little expansion or contraction when the heat-formable tubular member 23 is heat-formed onto the core member. A presently preferred material for forming the core member 10 from is Kovar stainless steel which is supplied by the Fry Steel Co. under ASTM specification F15-83. This material is provided with a heat treatment at 1250 degrees F. The Kovar steel is supplied as 0.35 inch diameter rounds. The ultimate strength thereof is about 80 ksi and the yield stress (0.2% offset) is about 62 ksi. The Kovar steel has a coefficient of expansion of about $4.9 \times 10^{-6}$ cm/cm/degrees C. The preferred solution for dissolving the Kovar core member is an acidic aqueous solution of iron chloride ($FeCl_3$) at a pH of about 1 to about 2. While an acidic solution of iron chloride is preferred, other solutions may be employed.

The presently preferred heat-formable tubular member from which the mold is made is formed from Pyrex (borosilicate) glass (Code No. 7740) supplied from the Corning Glass Works. The glass has a Youngs Modulus of about $6.6 \times 10^3$ kg/mm, a coefficient of expansion of about $35 \times 10^{-7}$ cm/cm/degree C. and a density of about 2.2 gm/cm$^3$. The inner diameter of the tubular glass member is slightly larger than the outer diameter of the core member 10 and in the presently preferred embodiment has a wall thickness of about 0.08 inch. The softening point of this glass, the temperature at which the glass tube is formed about the core member 10 into the mold is about 1000 degrees C.

The tubular holding members 13 and 14 are preferably gage pins (Meyer's minus series) formed of a stainless steel which has a Rockwell C hardness of about 60 to about 62 and have an ID of about 0.017–0.018 inch and an OD of about 0.033–0.034 inch.

Figure 7:
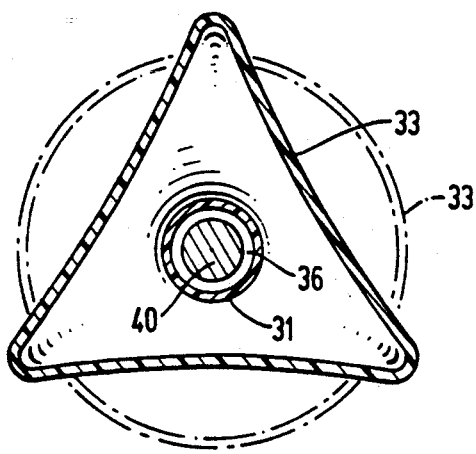
FIG. 7 is a cross-sectional view taken along the lines 7—7 shown in FIG. 6 with the interior of the balloon at atmospheric pressure.
Figure 8:
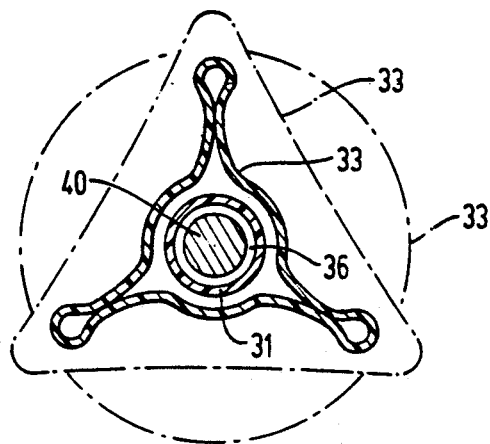
FIG. 8 is a transverse cross-sectional view taken along the lines 8—8 shown in FIG. 6 with the interior of the balloon under a vacuum.

Reference is made to FIGS. 6–8 which illustrate the distal end of a dilatation catheter assembly having a balloon which is readily made by the mold and method of the present invention. The catheter assembly shown generally includes an elongated catheter body 30 with an inner tubular member 31 and an outer tubular member 32 concentrically disposed about the inner tubular member and an inflatable balloon 33 with the proximal end thereof bonded to the distal end of the outer tubular member 32 and the distal end of the balloon bonded to the distal end of the inner tubular member 31. The guidewire 34 extends through the inner lumen 36 of the inner tubular member 31 and has a helical coil 37 secured to the distal portion which extends out of the distal end of the balloon 33. A rounded tip or plug 38 is provided at the distal end of the coil 37. The core wire 40 of the guidewire 34 may extend to the plug 38 and be secured thereto by suitable means or the core wire may terminate short of the plug with a shaping ribbon (not shown) extending to the plug 38.

The prism-like shape of the balloon 33 shown in FIGS. 6 and 7 is generally the formed shape of the balloon which is retained under ambient conditions. When the balloon 33 is subjected to internal pressures normally encountered in angioplasty procedures, e.g., 4 atmospheres or more, the balloon inflates into a circular cross-sectional shape, shown in phantom in FIG. 7. The balloon material is flexible but should be relatively inelastic so there is little or no radial expansion upon the inflation thereof.

When the interior of the triangular shaped balloon 14 is subjected to a vacuum to remove inflation fluid from the interior thereof, the balloon assumes a three wing cross-sectional shape as shown in FIG. 8. A slight radial shrinkage occurs when the interior of the balloon is subjected to a vacuum.

The balloon of the invention is preferably formed from a polyester resin such as polyethylene terephthalate (PET) having an intrinsic viscosity, a measure of its molecular weight, greater than 0.5, preferably about 0.7 to about 1.3. The tensile strength and thus the burst pressure of the balloon and the degree of biaxial orientation depends upon the starting intrinsic viscosity of the resin and the amount of work imparted to the polymer when the balloon is being formed. Typically, the intrinsic viscosity of the starting PET resin is about 0.95.

The resin of the desired intrinsic viscosity is extruded into a hollow tube having an outer diameter of about 0.015 to about 0.05 inch and an inner diameter of about 0.006 to about 0.03 inch. The tube is placed into a glass mold of the invention into the internal molding cavity having the desired triangular prism-like shape with one end of the tube closed off by a suitable clamp. The interior of the tube is then subjected to about 100 psi while the tube within the mold is heated, causing the tube to expand against the inner surface of the mold body and to thereby take the shape and dimensions of the inner molding surfaces of the mold. Longitudinal tension should be applied during the expansion and heating of the tube. Balloon tensile strengths in the hoop direction generally range from about 28,000 to about 32,000 psi. Balloon wall thickness typically ranges from about 0.00025 to about 0.002 inch for most angioplasty procedures. Deflated profiles generally are less than 0.050 inch. Typical inflated balloon diameters range from about 1.0 to about 10 mm for coronary angioplasty and up to 22 mm for peripheral angioplasty. The balloon length generally is much greater than the inflated radial dimension and typically is about 10 to 30 mm for coronary procedures and up to 10 cm for peripheral procedures.

While the presently preferred embodiment is described in terms of a triangular prism-like shape, other prism-like shapes, including those having square or hexagonal cross sections, can be employed to provide improved results, e.g., reduced profiles. Moreover, while the polyethylene terephthalate homopolymer is the only polymer specifically described herein, copolymers and mixtures or alloys with other polymers or even other polymer systems such as polyethylene may be employed without departing from the scope of the invention.

Moreover, the balloon mold of the present invention can be made of materials other than glass as will be recognized by those skilled in the art. For example, the heat-formable tubular member may be of a suitable plastic material. Similarly, the core member and other components may be formed from materials other than those described herein as preferred embodiments. Other modifications and improvements can be made to the invention without departing from the scope thereof.

What is claimed is:

1. A method of making a mold for forming small diameter inflatable members comprising:
   a) forming a core member having a shape and dimensions which correspond to the shape and dimensions of inflatable members to be molded and having an inner passageway extending therein which is in fluid communication with an opening at an end of the core member;
   b) inserting an end of an elongated holding member into the opening in an end of the core member;
   c) disposing the core member with the elongated holding member inserted within an end thereof within the interior of a heat-formable tubular member having proximal and distal ends;
   d) forming a mold by heating the heat-formable tubular member while applying a vacuum to the interior thereof to cause the heat-formable tubular member to be shaped about the core member and take the shape and dimensions of the exterior of the core member; and
   e) passing a solution through the inner passageway of the core member to thereby dissolve the core member to remove the core member from the interior of the mold.

2. The method of claim 1 wherein the heat-formable tubular member is made from heat formable glass.

3. The method of claim 2 wherein the glass ia borosilicate glass.

4. The method of claim 1 wherein the inner passageway of the core member passes through the entire length of the core member.

5. The method of claim 4 wherein core member is made from stainless steel.

6. The method of claim 5 wherein the solution for dissolving the core member is an acidic aqueous solution containing iron chloride.

7. The method of claim 6 wherein the pH of the aqueous solution ranges from about 1 to about 2.

8. The method of claim 1 wherein the holding members are removed from the mold after the core member is dissolved.

9. A method of forming a small diameter inflatable member comprising:
   a) forming a mold having an inner molding chamber with a continuous molding surface therein having the shape and dimensions of the desired inflatable member by the steps of,
       forming a core member having a shape and dimensions which correspond to the shape and dimensions of inflatable members to be molded and having an inner passageway extending therein which is in fluid communication with an opening at an end of the core member,
       inserting an end of an elongated holding member into the opening in an end of the core member,
       disposing the core member with the elongated holding member inserted within an end thereof within the interior of a heat-formable tubular member having proximal and distal ends
       forming a mold by heating the heat-formable tubular member while applying a vacuum to the interior thereof to cause the heat-formable tubular member to be shaped about the core member and take the shape and dimensions of the exterior of the core member, and
       passing a solution through the inner passageway of the core member to thereby dissolve the core member to remove the core member from the interior of the mold;
   b) inserting a tubular plastic member within the molding chamber;
   c) subjecting the plastic tubular member to internal fluid pressure and heat so that the tubular plastic member inflates within the molding chamber, engages the continuous molding surface of the molding chamber and thereby takes on the shape and dimensions thereof; and
   d) cooling the shaped plastic tubular member to retain the desired shape of the balloon therein.

* * * * *